US00PP16167P2

(12) United States Plant Patent
Gitzels

(10) Patent No.: US PP16,167 P2
(45) Date of Patent: Dec. 20, 2005

(54) ***DAHLIA* PLANT NAMED 'BALDELRASP'**

(50) Latin Name: *Dahlia variabilis*
Varietal Denomination: Baldelrasp

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 9 days.

(21) Appl. No.: 11/022,720

(22) Filed: Dec. 27, 2004

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—Wood, Phillips, Katz, Clark & Mortimer

(57) ABSTRACT

A new and distinct *Dahlia* plant named 'Baldelrasp', characterized by its burgundy-colored ray florets, yellow-colored disc florets, and upright, mounded growth habit.

2 Drawing Sheets

Latin name of genus and species of plant claimed: *Dahlia variabilis.*
Variety denomination: 'Baldelrasp'.

BACKGROUND OF THE INVENTION

The present invention relates to a new and distinct *Dahlia* plant botanically known as *Dahlia variabilis* and hereinafter referred to by the cultivar name 'Baldelrasp'.

The new cultivar originated in a controlled breeding program in Enkhuizen, The Netherlands during July 1997. The objective of the breeding program was the development of freely flowering *Dahlia* cultivars with large inflorescences and an upright growth habit.

The female parent of the new cultivar was the proprietary breeding selection designated 97.1358, not patented, characterized by its red-colored inflorescences. The male parent of the new cultivar was 'Dapadred', U.S. Plant Pat. No. 11,671, characterized by its red inflorescences and compact growth habit. Seed from the above stated cross-pollination was germinated and grown to maturity. One plant within the progeny was discovered and selected by the inventor during May 1998 at Enkhuizen, The Netherlands.

Asexual reproduction of the new cultivar by terminal stem cuttings taken since May 1998 at Enkhuizen, The Netherlands and West Chicago, Ill. has demonstrated that the new cultivar reproduces true to type, with all characteristics as herein described, firmly fixed and retained through successive generations of such asexual propagation.

SUMMARY OF THE INVENTION

The following characteristics of the new cultivar have been repeatedly observed and can be used to distinguish 'Baldelrasp' as a new and distinct cultivar of *Dahlia* plant:

1. Double burgundy-colored ray florets and yellow-colored disc florets.
2. Upright, mounded growth habit.

Plants of the new cultivar differ from plants of the female parent primarily in inflorescence color and from the male parent primarily in foliage size and ray floret color.

Of the many *Dahlia* cultivars known to the inventor, the most similar to the new cultivar is the cultivar Dapadred, U.S. Plant Pat. No. 11,671. However, in side by side comparisons, plants of the new cultivar differ from plants of 'Dapadred' in the following characteristics:

1. Plants of the new cultivar exhibit smaller foliage than the plants of 'Dapadred'.
2. Plants of the new cultivar exhibit lighter ray floret color than the plants of 'Dapadred'.

BRIEF DESCRIPTION OF THE PHOTOGRAPHS

The accompanying photographs show as nearly true as it is reasonably possible to make the same in color illustrations of this type, typical inflorescence and foliage characteristics of the new cultivar. Colors in the photographs differ slightly from the color values cited in the detailed description, which accurately describes the colors of the new cultivar. The plants were grown for 11 weeks in a greenhouse at West Chicago, Ill.

DETAILED BOTANICAL DESCRIPTION

Figure 1:
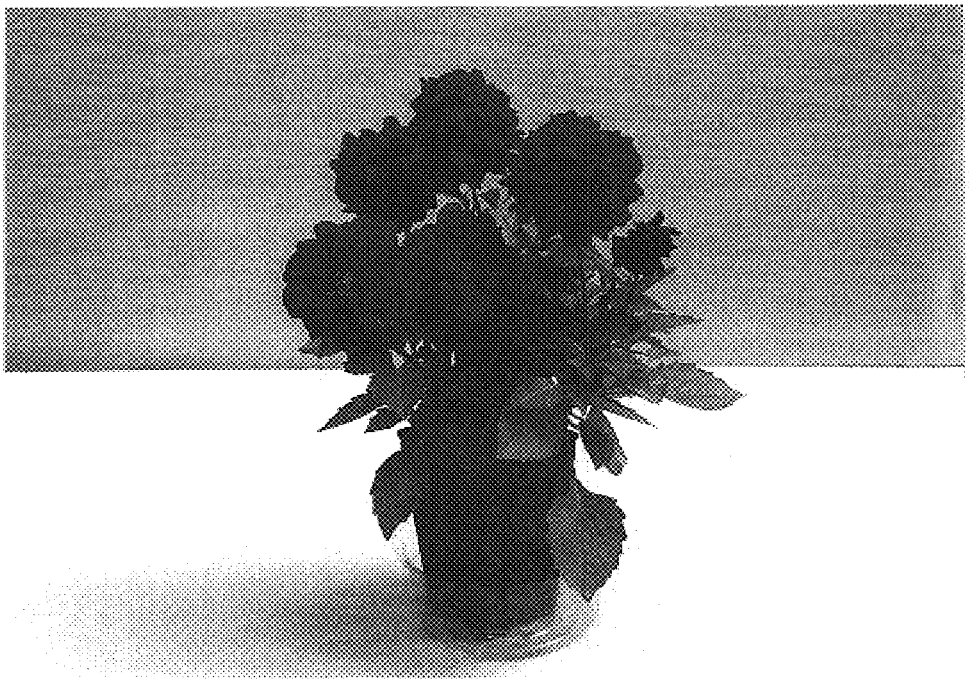
FIG. 1 illustrates a side view of the overall growth and flowering habit of 'Baldelrasp'.
Figure 2:
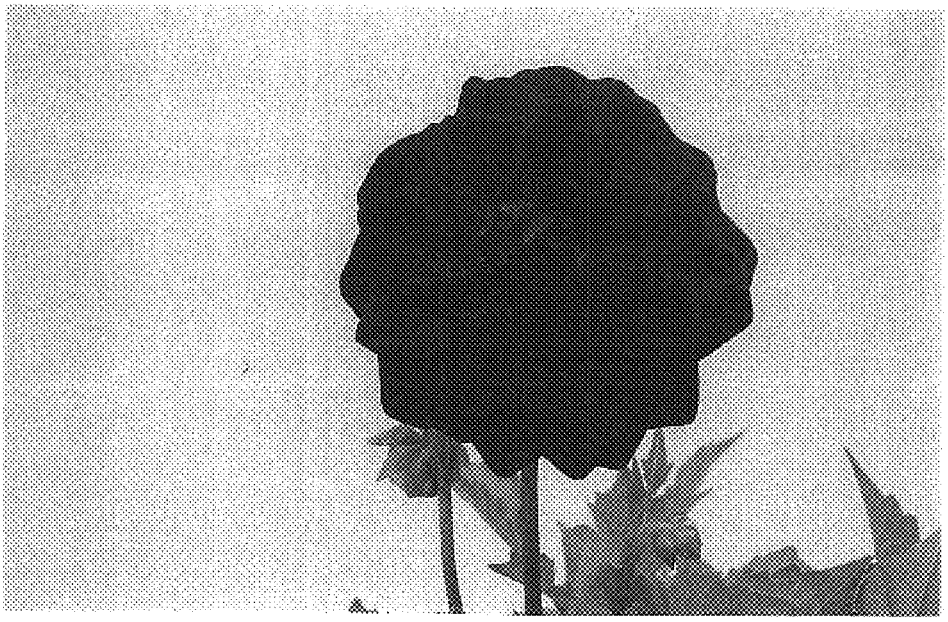
FIG. 2 illustrates a close-up view of a single inflorescence 'Baldelrasp' just opening.
Figure 3:
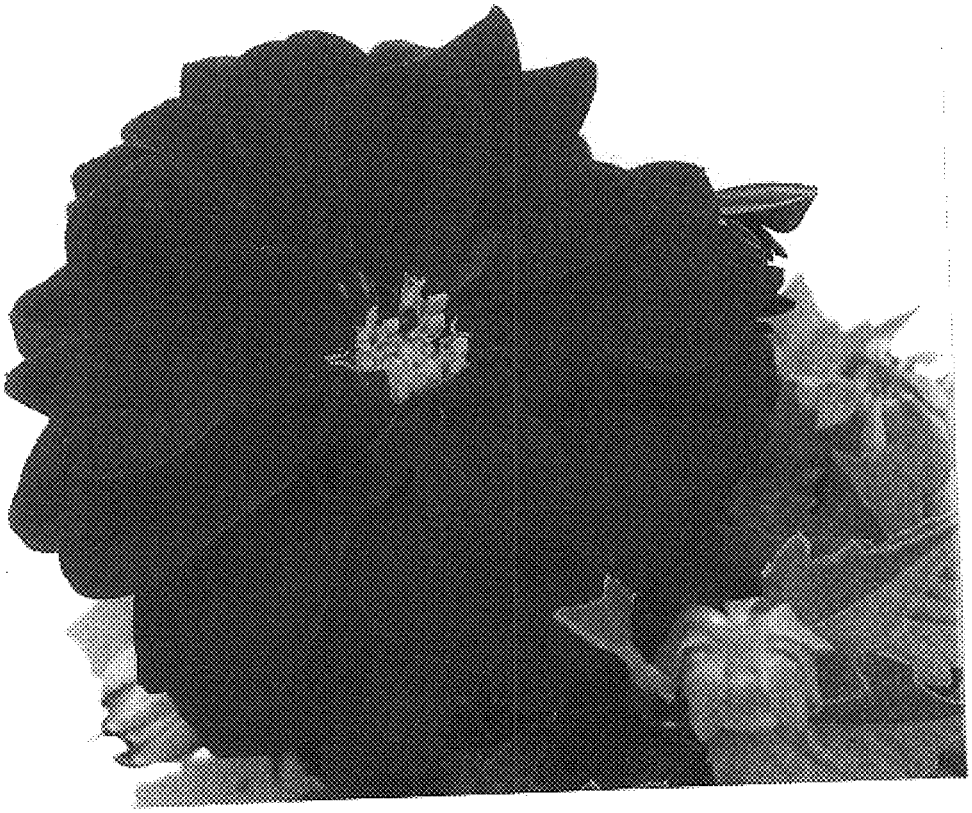
FIG. 3 illustrates a single fully open inflorescence of 'Baldelrasp'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 21, 2004 between 10:00 a.m. and 11:45 a.m. under natural light conditions in West Chicago, Ill.

The following descriptions and measurements describe plants produced from cuttings taken from stock plants and grown in a double polycarbonate-covered greenhouse in West Chicago, Ill. under conditions comparable to those used in commercial practice. The plants were grown in 10 cm pots for 11 weeks while utilizing a soil-less growth medium. Greenhouse temperatures were maintained at approximately 65°–75° F. (18°–24° C.) during the day and approximately 60°–65° F. (15°–18° C.) during the night. Greenhouse light levels were maintained at approximately 4,000–6,000 footcandles during the day. Plants were pinched three weeks after planting of rooted cuttings.

Botanical classification: *Dahlia variabilis* cultivar Baldelrasp.

Parentage:

*Female parent.*—Proprietary *Dahlia* breeding selection designated 97.1358, not patented.

*Male parent.*—*Dahlia* cultivar Dapadred, U.S. Plant Pat. No. 11,671.

Propagation:

*Type cutting.*—Terminal tip.

*Time to initiate roots.*—Approximately 7 to 10 days.

*Time to produce a rooted cutting.*—Approximately 21 to 28 days.

*Rooting habit.*—Freely branching.

*Root description.*—Fine, fibrous.

*Tubers.*—Will form under short day conditions of at least 13 to 14 hours of darkness.

Plant description:

*Crop time.*—Approximately 8–10 weeks.

*Growth habit.*—Basal branching, pinching enhances branching.

*General appearance and form.*—Upright, mounded, and vigorous.

*Size.*—Height from top of soil to top of plant plane: Approximately 24.1 cm. Width/area of spread: Approximately 25 cm.

*Branch description.*—Quantity per plant: Approximately 4. Strength: Strong. Length: Approximately 10.8 cm. Diameter: Approximately 5.3 mm. Length of center internode: Approximately 1.7 cm. Texture: Glabrous. Color: 144A.

*Foliage.*—Quantity of leaves per lateral branch: Approximately 12. Type: Compound and simple. Arrangement: Opposite. Aspect: At an acute angle to stem. Quantity of leaflets per leaf: 3 or 5. Leaf/leaflet: Shape: Ovate. Apex: Acuminate. Base: Cuneate. Margin: Dentate. Venation pattern: Pinnate. Length of mature compound leaves: Approximately 7 cm. Width of mature compound leaves: Approximately 8 cm. Length of petiole of compound leaf: Approximately 5.2 cm. Diameter of petiole of compound leaf: Approximately 2 mm. Length of terminal leaflet: Approximately 5.5 cm. Width of terminal leaflet: Approximately 3 cm. Length of petiole of terminal leaf: Approximately 2 cm. Length of lateral leaflet and single leaf: Approximately 4.6 cm. Width of lateral leaflet and single leaf: Approximately 2.5 cm. Texture of upper and lower surface of all foliage: Hispidulous, slightly rugose. Color of upper surface of mature foliage: Closest to 137B with venation of 146C. Color of lower surface of mature foliage: Closest to 137C.

Flowering description:

*Outdoor flowering habit.*—'Baldelrasp' is freely flowering under outdoor growing conditions with substantially continuous blooming from spring through autumn.

*Time to first flower.*—Approximately 8 weeks.

Inflorescence description:

*Appearance.*—Type: Composite. Form: Fully double, arising from leaf axils on strong peduncles, positioned just over the foliage. Disc and ray florets arranged acropetally on a capitulum. Persistent.

*Quantity per plant.*—Approximately 5 fully open at any one time.

*Lastingness of bloom.*—Approximately 4 weeks from first open ray floret to senescence.

*Shape/size.*—Hemispherical. Diameter: Approximately 9 cm. Depth: Approximately 4.1 cm. Disc diameter: Approximately 1 cm. Receptacle diameter: Approximately 1.5 cm. Receptacle height/depth: Approximately 4 mm. Receptacle color: 145C.

*Flower bud.*—Quantity showing color per plant: Approximately 2. Rate of opening: Approximately 2 weeks from first color to full bloom. Shape: Oblate. Bud just before color: Length: Approximately 1.5 cm. Width: Approximately 1.3 cm. Color: 151A. Bud at first color: Length: Approximately 2 cm. Width: Approximately 1.7 cm. Color: 53C.

*Fragrance.*—None.

*Ray florets.*—Quantity: Approximately 42 per inflorescence arranged in several whorls. Shape: Elongated, cupped. Apex: Emarginate to rounded. Base: Fused to form tube. Margin: Entire. Length: Approximately 4 cm. Width: Approximately 1.7 cm. Texture: Glabrous. Color of upper surface of ray florets before disc florets open: Closest to 59A. Color of lower surface of ray florets before disc florets open: Closest to 59C. Color of upper surface of ray florets of fully opened inflorescences: Alternating longitudinal areas of 53A and 53B. Color of lower surface of ray florets of fully opened inflorescences: Alternating longitudinal areas of 53C and 53D.

*Disc florets.*—Disc florets develop after most of the ray florets are fully open. Quantity: Approximately 35. Shape: Elongated, cylindrical. Apex: 5 acute tips. Length: Approximately 4.3 mm. Diameter at apex: Approximately 2 mm. Texture: Glabrous. Color: Transparent, 9A at apex, 150D at base.

*Peduncle.*—Strength: Strong. Aspect: Erect. Length: Approximately 10 cm. Diameter: Approximately 3 mm. Texture: Glabrous. Color: 144A with overlay of 59B.

*Phyllaries.*—Quantity: Approximately 8. Shape: Lanceolate. Apex: Acute. Base: Attenuate. Margin: Entire. Length: Approximately 8 mm. Width: Approximately 3 mm. Texture of upper surface: Glabrous. Color of upper and lower surfaces: 146B with parallel venation of 150A.

*Reproductive organs.*—Androecium — On disc florets. Stamen number: 4. Anther length: Approximately 3.3 mm. Anther color: 9A. Pollen amount: Abundant. Pollen color: 21A. Gynoecium — On disc and ray florets. Pistil quantity: One per floret. Pistil length: Approximately 1.1 cm. Stigma length: Approximately 3 mm. Stigma color: 9A. Style length: Approximately 6 mm. Style color: 150D. Ovary length: Approximately 2 mm. Ovary color: 145B.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldelrasp', substantially as herein shown and described.

* * * * *